United States Patent
Liao et al.

(10) Patent No.: US 12,279,811 B2
(45) Date of Patent: Apr. 22, 2025

(54) METHOD, APPARATUS AND ELECTRONIC DEVICE FOR CONTROLLING LASER SURGICAL INSTRUMENT

(71) Applicants: Suzhou Menovex Photonics Technology Co., Ltd, Suzhou (CN); Menovex Medical Technology (Shenzhen) Co., Ltd, Guangdong (CN)

(72) Inventors: Kuiyu Liao, Suzhou (CN); Yixiang Dai, Suzhou (CN); Encai Ji, Guangdong (CN); Liuzhu Li, Suzhou (CN)

(73) Assignees: Suzhou Menovex Photonics Technology Co., Ltd, Suzhou (CN); Menovex Medical Technology (Shenzhen) Co., Ltd, Shenzhen (CN)

(*) Notice: Subject to any disclaimer, the term of this patent is extended or adjusted under 35 U.S.C. 154(b) by 0 days.

(21) Appl. No.: 18/676,469

(22) Filed: May 28, 2024

(65) Prior Publication Data
US 2024/0307118 A1 Sep. 19, 2024

Related U.S. Application Data

(63) Continuation of application No. PCT/CN2022/126775, filed on Oct. 21, 2022.

(30) Foreign Application Priority Data

Nov. 29, 2021 (CN) .......................... 202111438656.8

(51) Int. Cl.
*A61B 18/20* (2006.01)
*G16H 40/63* (2018.01)
*A61B 18/00* (2006.01)

(52) U.S. Cl.
CPC ............. *A61B 18/20* (2013.01); *G16H 40/63* (2018.01); *A61B 2018/00702* (2013.01); *A61B 2018/00732* (2013.01)

(58) Field of Classification Search
CPC .......... A61B 18/20; A61B 2018/00702; A61B 2018/00732; G16H 40/63
(Continued)

(56) References Cited

U.S. PATENT DOCUMENTS

| 2013/0274644 A1 | 10/2013 | Hertz |
| 2023/0097906 A1* | 3/2023 | Shelton, IV ......... A61B 1/0638 606/1 |

FOREIGN PATENT DOCUMENTS

| CN | 108073545 A | 5/2018 |
| CN | 108303942 A | 7/2018 |

(Continued)

OTHER PUBLICATIONS

Machine translation of CN108073545A, published May 25, 2018, prepared Jun. 6, 2024, pp 1-11.
(Continued)

*Primary Examiner* — Aaron F Roane
(74) *Attorney, Agent, or Firm* — Addison D. Ault; IPGentleman Intellectual Property Services, LLC

(57) ABSTRACT

The present application provides a method, apparatus and electronic device for controlling laser surgical instruments; wherein the method comprises: obtaining a parameter information set for a target surgical procedure corresponding to the laser surgical instruments; performing optimization logic processing on the parameter information set based on the logical operation rules to obtain a target parameter set; wherein the target parameter set comprises target parameters corresponding to each of the laser surgical instrument; controlling each of the laser surgical instruments to operate (Continued)

S202 Obtaining a parameter information set for a target surgical procedure corresponding to the laser surgical instruments; wherein said parameter information set comprises parameter information for each of the laser surgical instruments S204 performing optimization logic processing on the parameter information set based on the logical operation rules to obtain a target parameter set S206 operate in accordance with the target parameters corresponding to each of the laser surgical instruments until the target surgical procedure is completed in accordance with the corresponding target parameters until the target surgical procedure is completed, in which the electronic device optimizes the parameter information set for the target surgical procedure by means of the logical operation rules and controls each of the laser surgical instruments to be operated in accordance with the corresponding target parameters.

8 Claims, 5 Drawing Sheets

(58) Field of Classification Search
USPC .................................................. 606/2
See application file for complete search history.

(56) References Cited

FOREIGN PATENT DOCUMENTS

| CN | 110553280 | A | 12/2019 |
|---|---|---|---|
| CN | 110788497 | A | 2/2020 |
| CN | 111796513 | A | 10/2020 |
| CN | 113608495 | A | 11/2021 |
| CN | 114153313 | A | 3/2022 |

OTHER PUBLICATIONS

Machine translation of CN108303942A, published Jul. 20, 2018, prepared Jun. 6, 2024, pp. 1-14.
Machine translation of CN110553280A, published Dec. 20, 2019, prepared Jun. 6, 2024, pp. 1-22.
Machine translation of CN110788497A, published Feb. 14, 2020, prepared Jun. 6, 2024, pp. 1-16.
Machine translation of CN113608495A, published Nov. 5, 2021, prepared Jun. 6, 2024, pp. 1-10.
Machine translation of CN114153313A, published Mar. 8, 2022, prepared Jun. 6, 2024, pp. 1-28.
Machine translation of CN111796513A, published Oct. 20, 2020, prepared Jun. 6, 2024, pp. 1-16.
PCT/CN2022/126775 International Search Report, issued Jan. 18, 2023, pp. 1-5 (original Chinese).
PCT/CN2022/126775 International Search Report, issued Jan. 18, 2023, pp. 1-3 (English translation accessed Jun. 6, 2024).
PCT/CN2022/126775 Written Opinion of the International Search Authority, issued Jan. 18, 2023, pp. 1-5 (original Chinese).
PCT/CN2022/126775 Written Opinion of the International Search Authority, issued Jan. 18, 2023, pp. 1-5 (English translation accessed Jun. 6, 2024).
CN202111438656.8 First Office Action dated Jul. 7, 2022, pp. 1-13 (original Chinese).
CN202111438656.8 First Office Action dated Jul. 7, 2022, pp. 1-12 (English Translation, generated May 15, 2024).
CNIPA Office Action, CN202111438656.8, Chinese language original, issued Jul. 7, 2021, pp. 1-13.
CNIPA Office Action, CN202111438656.8, issued Jul. 7, 2022, English machine translation generated Jan. 24, 2025, pp. 1-19.

* cited by examiner

METHOD, APPARATUS AND ELECTRONIC DEVICE FOR CONTROLLING LASER SURGICAL INSTRUMENT

CROSS-REFERENCES TO RELATED APPLICATIONS

The present application claims priority to Chinese patent application No. 2021114386568, filed with the Chinese Patent Office on Nov. 29, 2021, entitled "Method, apparatus and electronic device for controlling laser surgical instrument", the entire contents of which are incorporated herein by reference.

TECHNICAL FIELD

The present application relates to the field of laser medical technology, and in particular to method, apparatus and electronic device for controlling laser surgical instrument.

BACKGROUND TECHNOLOGY

With the development of laser technology, laser medical treatment has incomparable advantages with traditional medical treatment; specifically, laser surgery acts on the corresponding diseased tissues by utilizing the strong thermal effect of light energy, and its low-temperature thermal effect can reduce inflammation, stop bleeding, relieve pain, and regulate human body functions. At present, laser medical treatment mainly uses the thermal effect treatment method, the photochemical effect treatment method and medical instruments to realize laser surgery, wherein the medical instruments are usually equipped with a HMI (Human Machine Interface) screen and communicate with hardware such as the main control board and the laser emitter to realize laser surgery. Existing medical instruments mainly adopt development methodologies based on the underlying x86/64 system architecture, which can realize the communication and interaction function. However, it is common that there are many risk factors such as virus attack, crash, blue screen, etc., and it is impossible to recover quickly when an abnormality occurs, which reduces the efficiency and safety of laser surgery. With these reasons, existing methods mainly adopt the HMI screen control method, i.e., the HMI screen sends touch coordinate commands, and the MCU (Micro Control Unit) switches and adjusts between various displays on the HMI screen through a cumbersome set of commands to control the laser surgical instruments, which results in a long time-consuming process due to the large number of instruments in the laser surgery and thus reduces the efficiency of the laser surgery and cannot meet the practical application requirements.

SUMMARY

In view of the above, an object of the present application is to provide a method, apparatus and electronic device for controlling laser surgical instrument to alleviate the above problems which improve the operational efficiency of the laser surgical instruments and are of good practical value.

In a first aspect, embodiments of the present application provide a method of controlling a laser surgical instrument, applied to an electronic device equipped with an HMI screen; wherein the electronic device further comprises a controller and registers, wherein the controller is communicatively connected with the HMI screen, the registers, and the laser surgical instrument, respectively, and wherein the HMI screen is hard-decoupled with the laser surgical instrument, and wherein the controller is configured with logical operation rules, the logical operation rules are configured to represent direct logical operations between a variable storage address and the registers in the electronic device, and the method comprises: obtaining a parameter information set of a target surgical procedure corresponding to the laser surgical instrument; wherein the parameter information set comprises parameter information of each laser surgical instrument, the parameter information comprising: adjustable and non-adjustable parameters, and a first valid interval corresponding to the adjustable parameters and a second valid interval corresponding to the non-adjustable parameters; performing the optimization logic processing on the parameter information set based on the logic operation rules to obtain a target parameter set; wherein the target parameter set includes target parameters corresponding to each instrument; and controlling the operation of each instrument in accordance with the corresponding target parameters until the target surgical procedure is completed.

Optionally, the above parameter information set comprise an adjustable parameter set and a non-adjustable parameter set; the step of performing the optimization logic processing on the parameter information set based on the logical operation rules comprises: optimizing the adjustable parameter set based on the logical operation rules and the first valid interval set to obtain a target adjustable parameter set; wherein the target adjustable parameter set includes target adjustable parameters corresponding to each instrument, and the first valid interval set includes the first valid interval corresponding to each adjustable parameter in the adjustable parameter set; optimizing the non-adjustable parameter set based on the logical operation rules and the second valid interval set to obtain a target non-adjustable parameter set; wherein the target non-adjustable parameter set includes target non-adjustable parameters corresponding to each instrument, and the second valid interval set includes the second valid interval corresponding to each non-adjustable parameter in the non-adjustable parameter set.

Optionally, the above step of the parameter information set based on the logical operation rules further comprises: determining whether a constraint relationship exists between the adjustable parameters and the non-adjustable parameters in the parameter information set; if yes, performing the optimization logic processing on the parameter information set based on the logical operation rules and the constraint relationship to obtain the target parameter set.

Optionally, the above adjustable parameters comprise a first adjustable parameter and a second adjustable parameter, and the step of performing the optimization logic processing on the parameter information set based on the logical operation rules and the constraint relationship comprises: if the first adjustable parameter changes, determining an out-of-range direction of the non-adjustable parameters according to the second valid interval corresponding to the non-adjustable parameters, and carrying out a reverse calculation based on the out-of-range direction, the second adjustable parameter, and the constraint relationship, to obtain a target first adjustable parameter corresponding to the first adjustable parameter.

Optionally, the above step of performing the optimization logic processing on the parameter information set based on the logical operation rules further comprises: determining whether a constraint relationship exists between the adjustable parameters in the parameter information set; if yes, performing the optimization logic processing on the parameter information set based on the logical operation rules and the constraint relationship to obtain the target parameter set.

Optionally, the above adjustable parameters comprise a third adjustable parameter and a fourth adjustable parameter, and the step of performing the optimization logic processing on the parameter information set based on the logic operation rules and the constraint relationship further comprises: if the third adjustable parameter is changed, and, if the corresponding first valid interval is not exceeded, determining the out-of-range direction of the fourth adjustable parameter based on the corresponding first valid interval of the fourth adjustable parameter and determining a limit value at the out-of-range direction in the first valid interval corresponding to the fourth extreme adjustable parameter as a target fourth adjustable parameter corresponding to the fourth adjustable parameter.

Optionally, the step of performing the optimization logic processing on the parameter information set based on the logic operation rules further comprises: determining whether a constraint relationship exists between the non-adjustable parameters in the parameter information set; if yes, performing the optimization logic processing on the parameter information set based on the logical operation rules and the constraint relationship to obtain the target parameter set.

Optionally, the step of performing the optimization logic processing on the parameter information set based on the logic operation rules further comprises: determining whether constraint relationships exist between the adjustable parameters and the non-adjustable parameters in the parameter information set, and between the adjustable parameters; if yes, performing the optimization processing on the logic of the parameter information set based on the logical operation rules and the constraint relationships to obtain the target parameter set.

Optionally, the step of performing the optimization logic processing on the parameter information set based on the logic operation rules further comprises: determining whether constraint relationships exist between the adjustable parameters and the non-adjustable parameters in the parameter information set, and between the non-adjustable parameters; if yes, performing the optimization logic processing on the parameter information set based on the logical operation rules and the constraint relationships to obtain the target parameter set.

Optionally, the step of performing the optimization logic processing on the parameter information set based on the logic operation rules further comprises: determining whether constraint relationships exist between the adjustable parameters and the non-adjustable parameters, between the adjustable parameters and between the non-adjustable parameters in the parameter information set; if yes, performing the optimization logic processing on the parameter information set based on the logical operation rules and the constraint relationships to obtain the target parameter set.

Optionally, the method further comprises: obtaining an operation information set sent by the laser surgical instrument; wherein the operation information set comprises operation information sent by each instrument; determining target operation information based on priority information carried by each piece of the operation information; performing logical processing on the target operation information based on the logical operation rules and feeding back the processing results to a target instrument corresponding to the target operation information.

Optionally, the variable storage address comprise an alarm storage address, and the method further comprises: determining whether alarm information is an internal alarm when the alarm information is monitored in the alarm storage address; wherein the internal alarm is alarm information generated by the electronic device; if yes, generating an alarm processing instruction based on the logical operation rules, and processing the alarm information according to the alarm processing instruction; and, generating a reset instruction after the processing is completed, and sending the reset instruction to the alarm storage address to cause the alarm storage address to be cleared and reset in accordance with the reset instruction.

Optionally, the method further comprises: if the alarm message is a non-internal alarm, generating a blocking processing instruction based on the logical operation rules; wherein the non-internal alarm is an alarm message sent by the laser surgical instrument; sending the blocking processing instruction to a target register corresponding to the alarm storage address to cause the target register to be switched to a blocking state according to the blocking processing instruction; wherein the target register is a state memory register.

Optionally, after the target register is switched to the blocking state, the method further comprises: when the alarm clearing instruction sent by the laser surgical instrument is monitored, carrying out a clearing process of the alarm information based on the logical operation rules and the alarm clearing instruction; and, when the clearing process is completed, triggering the target register to be switched from the blocking state to the non-blocking state and generating a zeroing instruction, and sending the zeroing instruction to the target register, so as to cause the target register to carry out zeroing process based on the zeroing instruction.

In a second aspect, embodiments of the present application also provide a laser surgical instrument control apparatus applied to an electronic device configured with an HMI screen; wherein the electronic device further comprises a controller and a register, wherein the controller is communicatively connected to the HMI screen, the register, and the laser surgical instrument, respectively, and wherein the HMI screen and the laser surgical instrument are in a hard-decoupled relationship, and wherein the controller is configured with a logic operation rule, the logic operation rule configured to represent direct logical operations between the variable storage address and the register in the electronic device, and the apparatus comprises: a parameter acquisition module configured to obtain a parameter information set of the target surgical procedure corresponding to the laser surgical instrument; wherein the parameter information set includes parameter information of each laser surgical instruments, and the parameter information comprises: an adjustable parameter and a non-adjustable parameter, a first valid interval corresponding to the adjustable parameter and a second valid interval corresponding to the non-adjustable parameter; a logic processing module configured to perform an optimization logic processing on the parameter information set based on the logic operation rules to obtain the target parameter set; wherein the target parameter set comprises target parameters corresponding to each of the instruments; a control operation module configured to control the operation of each of the instruments in accordance with the corresponding target parameters until the target surgical procedure is completed.

In a third aspect, embodiments of the present application further provide an electronic device comprising a memory, a processor and a computer program stored on the memory which can be executed on the processor, the processor is configured to implement the steps of the method of the first aspect described above when executing the computer program.

In a fourth aspect, embodiments of the present application further provide a computer-readable storage medium, the computer-readable storage medium having a computer program stored thereon, when the computer program is executed by the processor, the steps of the method of the first aspect described above are performed.

Embodiments of the present application bring about the following beneficial effects:

Embodiments of the present application provide method, apparatus and electronic device for controlling laser surgical instruments that performs an optimization logic processing on the parameter information set of a target surgical procedure by means of logical operation rules and control the operation of each laser surgical instrument in accordance with the corresponding target parameters, which avoids frequent switching or operation of an HMI screen for controlling the laser surgical instrument, the operation efficiency of the laser surgical instrument is improved, and at the same time error rate of the laser surgical instruments is reduced; and, the electronic device implements the operation between the variable storage address and the register through logical operation rules, which not only improves the operation efficiency, but also avoids surgical risks caused by the blue screen and other problems, which improves the operation accuracy of the laser surgical instruments, and thus improves the safety of the laser surgical operation, and facilitates to promote and to implement in practical applications and has good practical value.

Other features and advantages of the present application will be set forth in the subsequent specification and, in part, will become apparent from the specification or will be understood by implementing the present application. The purposes and other advantages of the present application are realized and obtained in the structure particularly indicated in the specification and drawings.

In order to make the foregoing purposes, features and advantages of the present application more apparent and understandable, preferred embodiments are hereinafter described in detail as follows, in conjunction with the accompanying drawings.

DESCRIPTION OF DRAWINGS

In order to illustrate the technical solutions more clearly in specific embodiments or prior art of the present application, the following will briefly introduce the accompanying drawings that need to be used in the description of the specific embodiments or prior art, and it is obvious that the accompanying drawings in the following description are some of the embodiments of the present application, and for the person of ordinary skill in the field, other drawings can be obtained according to these drawings, without inventive effort.

SPECIFIC EMBODIMENTS

In order to make the purpose, technical solutions and advantages of the embodiments of the present application clearer, the technical solutions of the present application will be described clearly and completely in the following in connection with the accompanying drawings, and it is obvious that the described embodiments are a part of the embodiments of the present application and not all of the embodiments. Based on the embodiments in the present application, all other embodiments obtained by the person of ordinary skill in the field without inventive effort fall within the scope of protection of the present application.

In order to solve the problem that existing HMI screens control laser surgery with low efficiency, embodiments of the present application provide method, apparatus and electronic device for controlling laser surgical instrument, which improve the operation efficiency and operation accuracy of the laser surgical instruments, thereby improving the safety of laser surgery, and having good practical value.

Figure 1:
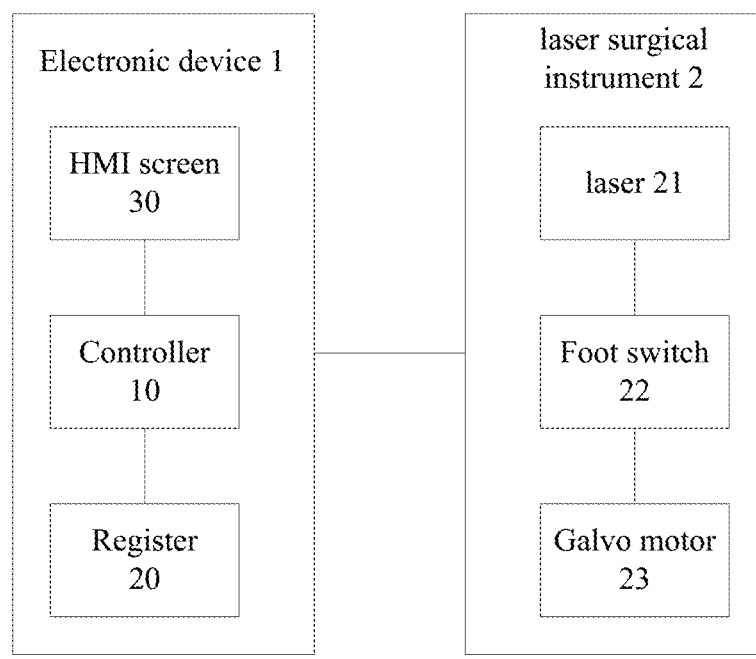
FIG. 1 is a diagram illustrating an application scenario of a laser surgical instrument provided by embodiments of the present application.

In order to facilitate the understanding of the present embodiments, the following will firstly describe a method for controlling a laser surgical instrument in detail provided by an embodiment of the present application. Therein, a laser surgical instrument application scenario diagram as shown in FIG. 1 comprises an electronic device 1 and a laser surgical instrument 2; wherein the electronic device 1 comprises a controller 10, and a register 20 and an HMI screen 30 communicatively connected to the controller 10; the controller 10 is also communicatively connected to the laser surgical instrument 2 in the laser surgery in practical applications, controlling the laser surgical instrument 2 to realize the laser surgery; and performing the direct logical operation between the variable storage address and the register 20 by means of logical operation rules.

Wherein, the aforesaid HMI screen 30 has a touch function and/or a floating touch function, and can also be connected with a mouse and a keyboard, etc., to facilitate manual operation of the HMI screen by a user, such as manual operation to switch the display page of the HMI screen, and modifying the contents of the display page, etc., specific settings can be made according to the actual situations, and the embodiments of the present application will not be limited to the description herein. The above-described laser surgical instrument 2 comprises, but is not limited to, hardware instruments such as the laser 21, a foot switch 22, and a galvo motor 23, which can be set up according to the actual situations.

In actual application, the above HMI screen 30 and the laser surgical instrument 2 have a hard decoupling relationship, which can be realized by direct logic operation between the variable storage address and the registers without relying on other peripherals, as follows:

(1) setting the set of all registers used for variable operations and logical decisions in the electronic device as $X=\{x_1, x_2, \ldots, x_n\}$; wherein $x_i$ represents the registers used for arbitrary variable operations and logical decisions, $i=1, 2, \ldots, n$; it should be noted that the variable operations and logical decisions here include but are not limited to service processing logic, functional page switching, error handling rollback, parameter reading and modification and other regular functional logic, and different functional logic processes by calling corresponding registers designated according to the code;

(2) setting the set of registers used for state memory as $R=\{r_1, r_2, \ldots, r_n\}$; wherein $r_i$ represents the registers used to store the state memory, $i=1, 2, \ldots, n$;

(3) setting the set of variable storage addresses as: $P=\{p_1, p_2, \ldots, P_n\}$; wherein $p_i$ represents any variable storage address, $i=1, 2, \ldots, n$; wherein multiple variable storage addresses can be ordered according to the complexity, and set the display widget corresponding to the variable storage address, etc., which can be set according to the actual situations;

(4) setting the set of values corresponding to the set of variable storage addresses as $*P=\{*p_1, *p_2, \ldots, *P_n\}$, wherein the set of values includes the values corresponding to each variable storage address in the set of variable storage addresses;

Through the setting operations of (1)-(4) above, the value $*p_i$ pointed by the variable storage address $p_i$ can be modified in accordance with specified communication protocols via peripheral hardware, for example, the peripheral hardware sends the operation information of $*p_i$ as a in accordance with the specified communication protocol, then the controller directly modifies $*p_i$ to a after receiving the operation information, and it can also be modified by passing the value through $x_i$, i.e. $x_i$ directly passes a to $*p_i$ and overwrites the original value of $*p_i$ according to the logical operation rules, thus realizing the modification of $*p_i$, and displaying through the HMI screen, thus to implement the hard decoupling relationship between the HMI screen and the peripheral hardware (laser surgical instruments).

In practical application, hard decoupling is the basis for the realization of collaborative computation and dynamic task allocation mechanism, which can realize the dynamic planning of the execution entity for each service function after complete operation. Based on the above hard decoupling relationship, the electronic device can build an efficient and reliable collaborative computation and task allocation mechanism, which improves the operational efficiency of the electronic device, and thus improves the operational efficiency of the laser surgical instruments.

Figure 2:
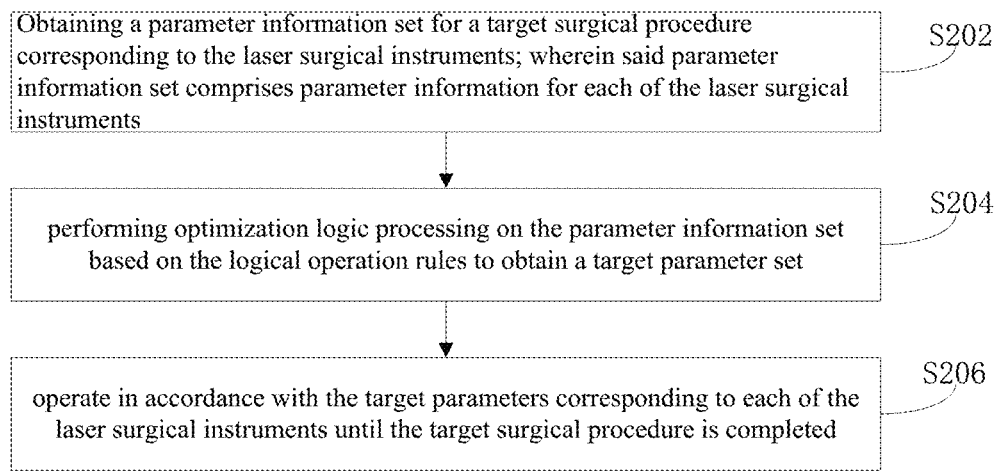
FIG. 2 is a flow chart of a method for controlling the laser surgical instrument provided by embodiments of the present application.

Based on the above electronic device, an embodiment of the present application provides a method for controlling a laser surgical instrument, the execution entity being a controller of the electronic device, as shown in FIG. 2, the method comprising the following steps:

Step S202, obtaining a parameter information set of a target surgical procedure corresponding to the laser surgical instrument; wherein the parameter information set comprises parameter information of each laser surgical instrument.

Specifically, in laser surgery, there may be a variety of surgical procedures, such as incision procedure, wrist debridement procedure, etc., which can be set according to the actual situations, and in practice, a set of surgical procedures including a variety of surgical procedures can be preselected and stored in the electronic device, such as setting a set of surgical procedures: $M=\{m_1, m_2, \ldots, m_n\}$; wherein, $m_1 \sim m_n$ represent different surgical procedures, and, different from each other, such as $m_1$ represents incision procedure, $m_2$ represents wrist debridement procedure, etc., which can be set according to the actual situations.

Before the laser surgery begins, the user may manually determine the target surgical procedure from the set of surgical procedures via the HMI screen, or manually input the target surgical procedure, or determine the target surgical procedure via peripheral hardware, or determine the target surgical procedure by receiving information sent from other mobile devices, such as a wireless mobile, etc., which are communicatively connected to the controller etc., how to determine the target surgical procedure may be set according to the actual situation.

After determining the above-described target surgical procedure, since the target surgical procedure may require a plurality of instruments in the laser surgical instruments, the target surgical procedure comprises parameter information, i.e., a parameter information set, of each instrument in the laser surgical instruments, and since each instrument in the target surgical procedure may not perform the same function, the parameter information of each instrument is not the same. In order to facilitate the elaboration, each parameter information herein is categorized into adjustable parameters and non-adjustable parameters. The adjustable parameters are used to represent the parameters that can be adjusted by the instrument, such as the output frequency of the laser, etc., and the non-adjustable parameters are used to represent the parameters that cannot be adjusted by the instrument, such as limit values of certain dynamics parameters of the instrument or results of fast transformations of certain important parameters by means of operators, including, but not limited to, calculating the energy density of the current laser finally focusing on the lesion area by means of plurality of optical parameters and peripheral hardware specifications etc. . . . The parameter information can be set according to the actual situation.

Considering that there are limits to the instruments in practice, in addition to the adjustable parameters and the non-adjustable parameters, the parameter information also includes a first valid interval corresponding to the adjustable parameters and a second valid interval corresponding to the non-adjustable parameters, and the specific first and second valid intervals can be set according to the actual situations, and the embodiments of the present application do not limit to the description herein.

It is to be noted that the aforesaid parameter information set may be pre-stored in the electronic device, and when the user determines the target surgical procedure by manual operation through the HMI screen, the parameter information set corresponding to the target surgical procedure can be obtained, or after the target surgical procedure has been determined, the user may manually input the parameter information set corresponding to the target surgical procedure through the HMI screen, the way of inputting the parameter information set may be set according to the actual situation.

Step S204: performing an optimization logic processing on the parameter information set based on the logic operation rules to obtain the target parameter set;

After obtaining the above parameter information set, since there may be a plurality of adjustable parameters and non-adjustable parameters in the parameter information of each instrument, and, each adjustable parameter corresponds to a first valid interval, and each non-adjustable parameter corresponds to a second valid interval, it is also necessary to optimize the adjustable parameters and the non-adjustable parameters to determine the target adjustable parameters corresponding to each adjustable parameter in the first valid interval, and the target non-adjustable parameters corresponding to each non-adjustable parameter in the second valid interval, i.e., the controller performs an optimization logic processing on the parameter information set based on the logic operation rules to obtain a target parameter set including the target parameters corresponding to each instrument, so as to enable each instrument to be operated in accordance with the corresponding target parameters.

In one alternative embodiment, the above parameter set includes an adjustable parameter set and a non-adjustable parameter set; wherein the adjustable parameter set includes the adjustable parameters of each instrument, and the non-adjustable parameter set includes the non-adjustable parameters of each instrument, e.g., for the target surgical procedure m, the adjustable parameter set of $m_i$ is set as $A_{m_i}=\{a_{m_i}^1, a_{m_i}^2, \ldots, a_{m_i}^n\}$, wherein $a_{m_i}^1$ represents the adjustable parameter 1 of the target surgical procedure $m_i$, $a_{m_i}^2$ represents the adjustable parameter 2 of the target surgical procedure $m_i$ and so on, $a_{m_i}^n$ represents the adjustable parameter n of the target surgical procedure $m_i$. It should be noted that the above adjustable parameters are not the same, such as $a_{m_i}^1$ represents the laser energy, $a_{m_i}^2$ represents the time of operation, etc., the specific adjustable parameters can be set according to the actual situation; and the non-adjustable parameter set is set as $B_{m_i}=\{b_{m_i}^1, b_{m_i}^2, \ldots, b_{m_i}^n\}$; wherein, $b_{m_i}^1$ represents the non-adjustable parameter 1 of the target surgical procedure $m_i$, $b_{m_i}^2$ represents the non-adjustable parameter 2 of the target surgical procedure $m_i$, and so on, $b_{m_i}^n$ represents the non-adjustable parameter n of the target surgical procedure $m_i$. It should be noted that each of the above non-adjustable parameters is different, such as $b_{m_i}^1$ represents the total laser energy, etc.; the specific non-adjustable parameters can be set according to the actual situation.

The above process of performing optimization logic processing on the parameter information set based on the logic operation rules comprises: optimizing the adjustable parameter set based on the logic operation rules and the first valid interval set to obtain the target adjustable parameter set; wherein the target adjustable parameter set comprises the target adjustable parameters corresponding to each instrument, and the first valid interval set includes the first valid interval corresponding to each adjustable parameter in the adjustable parameter set; optimizing the non-adjustable parameter set based on the logical operation rules and the second valid interval set to obtain the target non-adjustable parameter set; wherein the target non-adjustable parameter set comprises the target non-adjustable parameters corresponding to each instrument, and the second valid interval set comprises the second valid interval corresponding to each non-adjustable parameter in the non-adjustable parameter set. For example, for the above adjustable parameter set $A_{m_i}$, the corresponding first valid interval set is $C_{m_i}=\{c_{m_i}^1, c_{m_i}^2, \ldots, c_{m_i}^n\}$; wherein, $c_{m_i}^1$ represents the first valid interval of the adjustable parameter $a_{m_i}^1$ of the target surgical procedure $m_i$, $c_{m_i}^2$ represents the first valid interval of the adjustable parameter $a_{m_i}^1$ of the target surgical procedure $m_i$, and so on, $c_{m_i}^n$ represents the first valid interval of the adjustable parameter $a_{m_i}^n$ of the target surgical procedure $m_i$ for the adjustable parameter of the target surgical procedure $m_i$, the corresponding first valid interval comprises upper and lower limit values, wherein $\max(a_{m_i}^j)=c_{m_i}^{2j-1}$, i.e. the adjustable parameter $a_{m_i}^j$ has the upper limit values $c_{m_i}^{2j-1}$, herein $c_{m_i}^{2j-1}$ represents odd numbers in the set $C_{m_i}$. Similarly, $\min(a_{m_i}^j)=c_{m_i}^{2j}$, i.e. the adjustable parameter $a_{m_i}^j$ has the lower limit values $c_{m_i}^{2j}$, herein $c_{m_i}^{2j}$ represents even numbers in the set $C_{m_i}$, and the order in which they are stored is related to the order of the adjustable parameter $a_{m_i}^j$ itself in the set. It should be noted that the first valid interval corresponding to each of the above adjustable parameters can be determined by the macro to specify the parameter accuracy and the maximum range, and should be determined by the correct accuracy in the correct range. The first valid interval corresponding to each of the adjustable parameters can be set according to the actual situation.

Similarly, for the above non-adjustable parameter set $B_{m_i}$, the corresponding second valid interval set is $D_{m_i}=\{d_{m_i}^1, d_{m_i}^2, \ldots, d_{m_i}^n\}$; wherein, $d_{m_i}^1$ represents the second valid interval of the non-adjustable parameter $b_{m_i}^1$ of the target surgical procedure $m_i$, $d_{m_i}^2$ represents the second valid interval of the non-adjustable parameter $b_{m_i}^n$ of the target surgical procedure $m_i$, and so on, $d_{m_i}^n$ represents the second valid interval of the non-adjustable parameter $b_{m_i}^n$ of the target surgical procedure $m_i$; for the non-adjustable parameter $b_{m_i}^j$ of the target surgical procedure $m_i$, the corresponding second valid interval comprises upper and lower limit values, wherein, $\max(b_{m_i}^j)=d_{m_i}^{2j-1}$, i.e., the non-adjustable parameter $b_{m_i}^j$ has the upper limit values $d_{m_i}^{2j-1}$, herein $d_{m_i}^{2j-1}$ represents odd numbers in the set $D_{m_i}$. Similarly, $\min(b_{m_i}^j)=d_{m_i}^{2j}$, i.e. the adjustable parameter $b_{m_i}^j$ has the lower limit values $d_{m_i}^{2j}$, herein $d_{m_i}^{2j}$ represents even numbers in the set $D_{m_i}$, and the order in which they are stored is related to the order of the adjustable parameter $b_{m_i}^j$ itself in the set.

Thus, by optimizing the adjustable parameter set by means of the logical operation rules and the first valid interval set, the target adjustable parameter set including the adjustable parameter set corresponding to each instrument can be obtained; and by optimizing the non-adjustable parameter set by means of the logical operation rules and the second valid interval set, the target non-adjustable parameter set including the target non-adjustable parameter set corresponding to each instrument can be obtained, so as to control each instrument to be operated in accordance with the corresponding target adjustable parameters and target non-adjustable parameters.

In addition, for the adjustable and non-adjustable parameters corresponding to each instrument, there are a pair of limit values (i.e., the upper and lower limits of the valid interval), which form a parity pair sequence and are stored in a specified area of the variable storage address set P. Since in majority of cases, the elements in the non-adjustable parameter set $B_{m_i}$ and the adjustable parameter set $A_{m_i}$ have a cross-computation relationship, if the result of the operation is intersected with the maximum range, a consistent valid interval can be generated, but the disadvantages are also obvious, i.e., the upper limit of the instrument's capability is lowered and the possibility of surgical scientific research is reduced. Therefore, the values of some elements in the second valid interval set $D_{m_i}$ and the first valid interval set $C_{m_i}$ will inevitably change with the change of the values of the corresponding elements in $B_{m_i}$ and $A_{m_i}$, thus achieving the effect of dynamic constraints.

Based on the above dynamic constraint relationship, in another alternative embodiment, the above-mentioned process of performing optimization logic processing of the parameter information set based on logical operation rules also includes: determining whether there is a constraint relationship in the parameter information set; wherein the constraint relationship includes: there is a constraint relationship between adjustable parameters and non-adjustable parameters, and/or there is a constraint relationship between adjustable parameters, and/or there is a constraint relationship between non-adjustable parameters; if yes, performing optimization logic processing on the parameter information set to obtain the target parameter set based on the logical operation rules and constraint relationships. It should be noted that the above-mentioned adjustable parameters and/ or non-adjustable parameters with constraint relationships can be parameters of the same device or parameters of different devices, the adjustable parameters and non-adjustable parameters can be set according to the actual situation.

The above-mentioned constraint relationship therein may be a forward constraint relationship or a reverse constraint relationship. For ease of understanding, some examples are provided herein, specifically:

constraint example (1): a dynamic constraint of a non-adjustable parameter $b_{m_i}^{\ l}$ on two different adjustable parameters $a_{m_i}^{\ j}$ and $a_{m_i}^{\ k}$: $f_0(a_{m_i}^{\ j}, a_{m_i}^{\ k})=b_{m_i}^{\ l}$;

constraint example (2): a dynamic constraint of one adjustable parameter $a_{m_i}^{\ q}$ on another adjustable parameter $a_{m_i}^{\ j}$. The upper limit value of the adjustable parameter $a_{m_i}^{\ j}$ is $c_{m_i}^{\ 2j-1}$, and the lower limit value is $c_{m_i}^{\ 2j}$, i.e. $f_1(a_{m_i}^{\ q})=c_{m_i}^{\ 2j-1}$, $f_2(a_{m_i}^{\ q})=c_{m_i}^{\ 2j}$;

constraint example (3): a direct constraint of a non-adjustable parameter by on an adjustable parameter $a_{m_i}^{\ j}$. For example, the lower limit value of the non-adjustable parameter determines the lower limit value of the adjustable parameter, and the upper limit value of the non-adjustable parameter determines the upper limit value of the adjustable parameter, i.e. $f_3(d_{m_i}^{\ 2s-1})=c_{m_i}^{\ 2k-1}$, $f_4(d_{m_i}^{\ 2s})=c_{m_i}^{\ 2k}$;

It should be noted that the above constraint example (3) can also be combined with the constraint example (1) to indirectly dynamically constrain another adjustable parameter, that is, it may include a combination of multiple constraint relationships, which can be set according to the actual situation. In addition, the specific form of the above operator $f_i$ can be set according to the actual situation, such as transformation, operation, amplification and other conventional constraint relationships.

For the above scenarios where constraint relationships exist, if the parameters that have not had error checking and correction are blindly sent, there would be high risk and great redundancy, therefore, it is necessary to perform the optimization logic processing on the parameter information set based on the logical operation rules and the constraint relationships to obtain the target parameter set. Specifically, removing redundancy by means of automatic error correction and communication based on the state memory mechanism, dynamically storing all the constrained adjustable parameters $a_{m_i}^{\ i}$, in the corresponding state memory register $r_i$, for example:

in constraint example (1), the adjustable parameters comprise a first adjustable parameter $a_{m_i}^{\ j}$ and a second adjustable parameter $a_{m_i}^{\ k}$, and if the first adjustable parameter $a_{m_i}^{\ j}$ is changed, determining an out-of-range direction of the non-adjustable parameter $b_{m_i}^{\ l}$ according to the second valid interval corresponding to the non-adjustable parameter $b_{m_i}^{\ l}$, and performing inverse calculation according to out-of-range direction, the second adjustable parameter $a_{m_i}^{\ k}$, and the constrained relationship to obtain the target first adjustable parameter corresponding to the first adjustable parameter $a_{m_i}^{\ j}$. Specifically, after the first preset value is calculated by the operator $f_0$, $a_{m_i}^{\ j}$ is stored in $r_j$, and $a_{m_i}^{\ k}$ is stored in $r_k$, and when the value of $a_{m_i}^{\ j}$ or $a_{m_i}^{\ k}$ changes every time, and, $b_{m_i}^{\ l}=[d_{m_i}^{\ 2l}, d_{m_i}^{\ 2l-1}]$, that is, the non-adjustable parameter $b_{m_i}^{\ l}$ is within its upper and lower limits, the changed values of $a_{m_i}^{\ j}$ and $a_{m_i}^{\ k}$ will be overwritten in $r_j$ and $r_k$, respectively, so as to carry out state memorization for the last correct values used at present; and if $b_{m_i}^{\ l} \neq [d_{m_i}^{\ 2l}, d_{m_i}^{\ 2l-1}]$ appears, that is, the non-adjustable parameter $b_{m_i}^{\ l}$, is not within its upper and lower limits, then compare the current instantaneous value of $a_{m_i}^{\ j}$ with $r_j$. If the current instantaneous value is not equal to $r_j$ (i.e., the value of $a_{m_i}^{\ j}$ has been modified so that $b_{m_i}^{\ l}$ exceeds the upper and lower limits), and obtain the limit value of $a_{m_i}^{\ j}$ in reverse according to operator $f_0$ trough the out-of-range direction of $b_{m_i}^{\ l}$ and $r_k$, i.e., the limit value of $a_{m_i}^{\ j}$ that can be obtained if $b_{m_i}^{\ l}$ does not exceed the upper and lower limits, and assign to $a_{m_i}^{\ j}$, and override $r_j$; on the contrary, the current instantaneous value of $a_{m_i}^{\ k}$ is compared with $r_k$, and the extreme value of $a_{m_i}^{\ k}$ is obtained in reverse according to the operator $f_0$ trough the out-of-range direction of $b_{m_i}^{\ l}$ and $r_j$, i.e., the extreme value of $a_{m_i}^{\ k}$ that can be obtained if $b_{m_i}^{\ l}$ does not exceed the upper and lower limits, then assign to $a_{m_i}^{\ k}$, and override $r_k$;

In constraint example (2), the adjustable parameters include the third adjustable parameter $a_{m_i}^{\ q}$ and the fourth adjustable parameter $a_{m_i}^{\ j}$. If the third adjustable parameter $a_{m_i}^{\ q}$ has been changed and does not exceed the corresponding first valid interval, determining an out-of-range direction of the fourth adjustable parameter $a_{m_i}^{\ j}$, and determining the extreme value corresponding to the out-of-range direction in the first valid interval corresponding to the fourth adjustable parameter $a_{m_i}^{\ j}$ as a target fourth adjustable parameter corresponding to the fourth adjustable parameter $a_{m_i}^{\ j}$. The target fourth adjustable parameter. Specifically, after the first preset value has been calculated by operators $f_1$ and $f_2$. $a_{m_i}^{\ q}$ will be stored in $r_q$, $a_{m_i}^{\ j}$ will be stored in $r_j$, and when $a_{m_i}^{\ q} \neq r_q$ (i.e. the current instantaneous adjustable parameter $a_{m_i}^{\ q}$ is not the same as the value in the corresponding state memory register $r_q$, which means that the value of $a_{m_i}^{\ q}$ has been modified) and has not exceeded the extreme value, the calculation will be re-performed via operators $f_1$ and $f_2$ and the transformed value is overwritten in $r_q$, i.e. the state memory register will be updated, and as a result of the calculations of the operators $f_1$ and $f_2$, if a, i.e. the adjustable parameters $a_{m_i}^{\ j}$ is out of the range, then determine the out-of-range direction, reassign the extreme value close to the out-of-range direction to $a_{m_i}^{\ j}$ and overwrite the value to $r_j$. When $a_{m_i}^{\ j} \neq r_j$ (i.e. the current instantaneous adjustable parameter $a_{m_i}^{\ j}$, is not the same as the value in the corresponding state memory register $r_j$, which means $a_{m_i}^{\ j}$ has been modified), if $a_{m_i}^{\ j} = [c_{m_i}^{\ 2j}, c_{m_i}^{\ 2j-1}]$, then overwrite the value of $a_{m_i}^{\ j}$ to $r_j$, i.e. when the adjustable parameter $a_{m_i}^{\ j}$ is not out of the range but has been adjusted, then overwrite the newest value of $a_{m_i}^{\ j}$ to $r_j$ thus to update and save it; if $a_{m_i}^{\ j} \neq [c_{m_i}^{\ 2j}, c_{m_i}^{\ 2j-1}]$, i.e. the adjustable parameter $a_{m_i}^{\ j}$ is out of the range, then according to the out-of-range direction, $a_{m_i}^{\ j}$ is regarded as an extreme value, and then obtaining $a_{m_i}^{\ q}$ in reverse with calculation by the operators $f_1$ or $f_2$, when $a_{m_i}^{\ q} = [c_{m_i}^{\ 2q}, c_{m_i}^{\ 2q-1}]$ is met, overwrite the extreme value $a_{m_i}^{\ j}$ to $r_j$, and overwrite $a_{m_i}^{\ q}$ to $r_q$. That is, when $a_{m_i}^{\ q}$ is obtained in reverse to be not out of the range, the parameter is correct, and the parameter will be directly overridden to the corresponding state memory register for updating. If $a_{m_i}^{\ q} = [c_{m_i}^{\ 2q}, c_{m_i}^{\ 2q-1}]$ is not met, according to the extreme value of the out-of-range direction of $a_{m_i}^{\ q}$, the value of $a_{m_i}^{\ j}$ should be calculated by the operators $f_1$ or $f_2$, and rolled back, i.e., when $a_{m_i}^{\ q} = [c_{m_i}^{\ 2q}, c_{m_i}^{\ 2q-1}]$) is not met, since it is caused due to $a_{m_i}^{\ j} \neq r_j$ that is, it is not met due to changes of $a_{m_i}^{\ j}$, $a_{m_i}^{\ j}$ needs to rolled back after calculation.

In constraint example (3), the first preset value $a_{m_i}^{\ k}$ is stored in $r_k$, when $(a_{m_i}^{\ k} \neq r_k) \wedge (a_{m_i}^{\ k} = [c_{m_i}^{\ 2k}, c_{m_i}^{\ 2k-1}])$ is true, that is, the adjustable parameter $a_{m_i}^{\ k}$ is not equal to the data or state last recorded in $r_k$, and the parameter range of $a_{m_i}^{\ k}$ is not out of the range, so the current value of $a_{m_i}^{\ k}$ is overwritten in $r_k$; when $(a_{m_i}^{\ k} \neq r_k) \wedge (a_{m_i}^{\ k} \neq [c_{m_i}^{\ 2k}, c_{m_i}^{\ 2k-1}])$ is true, the value of $a_{m_i}^{\ k}$ will be updated to the extreme value close to the out-of-range direction according to the out-of-range direction of $a_{m_i}^{\ k}$. If $b_{m_i}^{\ s}$ belong to changeable non-adjustable parameters, i.e., $b_{m_i}^{\ s}$ and $d_{m_i}^{\ 2s}$ will be changed, causing the value of $c_{m_i}^{\ 2k-1}$ and $c_{m_i}^{\ 2k}$ obtained by operators $f_3$ or $f_4$ to be changed at the same time, then it can be processed similar to the way in the constraint example (2), and the extreme value of $b_{m_i}^{\ s}$ can be obtained in inverse by the operators $f_3$ or $f_4$ thus to constraint $a_{m_i}^{\ k}$, i.e., since $b_{m_i}^{\ s}$ can be modified in this situation, it can be processed in a similar way of the adjustable parameter.

It should be noted that for other forms of constraint relationships, i.e., constraint examples, reference can be made to the above optimization logic processing of the three constraint examples, the embodiments of the present invention will not be described in detail herein.

In order to facilitate understanding, here is an example. For example: the current power value $P_{current}$=single pulse energy E*frequency F, that is, the value of $P_{current}$ is the product of E and F, then the arithmetic relationship between the three is the operator f, which is $f(E,F)=P_{current}$, wherein, E, F are adjustable parameters, $P_{current}$ is a non-adjustable parameter, so the above operator $f_i$ only needs to meet the constraint relationship between the adjustable parameters and non-adjustable parameters, the specific process is described as follows: ① calculate according to is $f(E,F)=P_{current}$; ② determine whether the current power value is between the maximum power and the minimum power, if yes, repeat step ①, and performing state memory for the parameters in the operator f, if no, then execute step ③; ③ determine whether adjusting the single-pulse energy E will cause the current power to be too large or too small by comparing the current value of the single-pulse energy E and the last value of the single-pulse energy E that is used and is stored in the state memory register, and if yes, select the maximum power or minimum power according to the out-of-range direction, and calculate an extreme single pulse energy within the range of the limit according to the selected power value and the corresponding frequency F (i.e., the last value that is used and memorized in the state memory register). ④ If it is no in step ③, follow the method in step ③ to determine whether adjusting the frequency causes the power value to be too large or too small, and take corresponding optimization processing; ⑤ When the above steps ③ and ④ are completed, perform the calculation in step ① again; ⑥ Detect the current duty cycle slot, and determine whether the current frequency is greater than the maximum frequency of the current duty cycle slot, if yes, then cancel the current duty cycle slot directly and use a slot with a larger duty cycle; ⑦ If no in the above step ⑥, determine whether the current frequency is less than the minimum frequency of the current duty cycle slot, if yes, then directly cancel the current duty cycle slot, use a slot with a smaller duty cycle; ⑧ refresh the currently used duty cycle slot, enable its corresponding maximum power and minimum power, so as to achieve the optimization processing of the adjustable parameters and the non-adjustable parameters through the constraint relationships (including the constraint examples and/or combination of the constraint examples between the adjustable parameters and non-adjustable parameters).

In practice, in a laser surgery procedure, the parameter information set usually comprises multiple (e.g., 5~10) parameter information, the parameter information has a strong correlation between each other, the above constraint examples can be combined and nested to derive more complex dynamic constraint relationships, so as to solve corresponding correlated problems in accordance with different situations, and through the constraints, some parameters of the laser surgery procedure which the surgery itself does not care about can be hidden, performing black box operations, which not only ensures the stability of the laser surgical instruments, but also realizes the simplicity effect of the HMI screen.

Step S206, controlling each instrument to operate in accordance with the corresponding target parameters until the target surgical procedure is completed.

The method for controlling laser surgical instrument provided by the embodiments of the present application perform optimization logic processing on the parameter information on of the target surgical procedure by means of the logic operation rules, and controls each laser surgical instrument to operate in accordance with the corresponding target parameters, which avoids frequent switching or operation of the HMI screen in order to control the laser surgical instrument, which improves the operation efficiency of the laser surgical instrument, and at the same time reduces the error rate of the laser surgical instrument. Furthermore, the electronic device realizes the operation between the variable storage address and the register by means of the logical operation rules, which not only improves the operation efficiency, but also avoids the surgical risks caused by the blue screen and other problems, thus improving the operation precision of the laser surgical instruments, and thus improving the safety of the laser surgery, which is easy to promote and implement in the practical application, and which has a good practical value.

Further, the above electronic device can also realize collaborative computation and task allocation, the specific process is elaborated in the following:

(1) Firstly, in the initialization stage of the system, for the register set R used for state memory, the variable storage address set P and the elements in the value set *P shall be cleared to zero, and if a part of $*p_i$ need to contain an initial value, the value of $*p_i$ shall be modified by passing the value through $x_i$ in this stage or the initial value shall be assigned by means of powering up and loading the configuration file;

(2) When the logic of display operation is involved, the address $p_i$ used by the display widget is determined and the value of $*p_1$ is modified by passing the value through $x_i$, and the controller completes the internal closed-loop operation based on the logical operation rules and displays it on the HMI screen, and, during the process, there is no need to trigger an interrupt for each instrument having the electronic devices for the collaborative computation work;

(3) When there are strong priority operations such as feedback or alarm from the collaborative computing of instruments, the instrument uploads the alarm information to the alarm storage address $p_j$ to synchronize, thus the task allocation of the alarm task processing is directly complemented; then the instrument can directly perform its own operations, and through the entire operation cycle, the controller will query the value $*p_j$ corresponding to the alarm address, as well as the value corresponding to alarm page address when there is alarm information overrides the value of display page address on the HMI to complete a forced jumping, i.e., when the alarm information appears, the current display page of the HMI screen is forced to switch to the alarm page and alarms in accordance with a preset form, so as to remind the user or the maintenance personnel to deal with it. Wherein, the preset form includes a text form and/or a voice form and/or an indicator form, which can be set according to the actual situation.

Optionally, the method further comprises: obtaining an operation information set sent by the laser surgical instruments; wherein the operation information set comprises operation information sent by each of the laser surgical instruments; determining target operation information based on priority information carried by each piece of the operation information; performing logical processing on the target operation information based on the logical operation rules, and feeding the processing results back to the target instrument corresponding to the target operation information. Specifically, due to the large number of instruments in the laser surgical instruments, in order to ensure the normal operation of the laser surgery, the operation information of each instrument is also configured with priority information, which can be set in accordance with the order of operation of each instrument during the surgical process, or in accordance with the importance of each piece of the operation information, the priority information can be set according to the actual situation. Thus, when the controller receives the operation information sent by the plurality of instruments, it first determines the target operation information from the operation information sent by the plurality of instruments according to the priority information, and then performs logical processing on the target operation information based on the logical operation rules, thereby improving the operation efficiency and accuracy of the laser surgery.

Furthermore, in practical application, each piece of the above operation information may also not carry the priority information, and in the logical operation rules, an operation code corresponding to each piece of the operation information is set, and a priority order of each operation code is set, and when performing the logical processing on the target operation information based on the logical operation rules, the operation information is processed according to the priority order of the operation code corresponding to each piece of the operation information. It is to be noted that each of the above operation information may be different types of the operation information sent by the same instrument, the same type of operation information sent by different instruments, or different types of the operation information sent by different instruments, etc., the operation information may be set according to the actual situation, and the embodiments of the present application do not provide a limiting description thereof.

(4) It is also necessary to adopt a state memory mechanism for high priority operations such as alarms, wherein the variable storage address comprises a pre-set alarm storage address, and the method further comprises: determining whether the alarm information is an internal alarm when the alarm information is monitored to be at the alarm information address; wherein the internal alarm is the alarm information generated by the electronic device; if yes, generating an alarm processing instruction based on the logical operation rules , and processing the alarm information according to the alarm processing instruction; and, generating a reset instruction after the processing is completed, and sending the reset instruction to the alarm storage address to cause the alarm storage address to be cleared and reset according to the reset instruction. Specifically, if the alarm information is an internal alarm generated by the electronic device, such as an internal alarm generated by a user who touches a button on the HMI screen by mistake, etc., then the electronic device may process the alarm information on its own, i.e., generating the alarm processing instruction based on the logical operation rules, and processing the alarm information according to the alarm processing instruction, and clearing and resetting the alarm storage address directly after the processing is completed.

The method further comprises: generating a blocking processing instruction based on the logical operation rules if the alarm information is a non-internal alarm; wherein the non-internal alarm is the alarm information sent by the laser surgical instrument; the controller sends the blocking processing instruction to a target register corresponding to the alarm storage address, for example, the controller sends the blocking processing instruction to the alarm storage address for storage, and the target register obtains from the alarm storage address the blocking processing instruction, and switches to the blocking state according to the blocking processing instruction; wherein the target register is a state memory register.

To facilitate understanding, an example is provided herein. Define $r_a$ as the target register corresponding to the alarm storage address, the target register is used to record the alarm status processing results of the alarm information. If the alarm status processing results are not processed, the target register $r_a$ will continue to maintain the blocking state in order to block the useless logic processing and redundant communication, and dynamic plan for the implementation of the various functional modules. All the interactive touch controls on the HMI screen adopt the $p_1$ return assignment method. Performing logic branch judgment according to $*p_1$ to realize listening of different buttons, at the same time in combination with the state memory mechanism method of the high priority operations of $r_a$, part of the buttons being listened can be blocked to avoid mis-operations and incorrect operations, so as to reduce redundant communication and the risk of errors.

In summary, the above automatic error correction and communication de-redundancy method based on the state memory mechanism has outstanding advantages in functions such as the adjustment of surgical parameters and the control of various functions etc., since the surgical parameters of the laser surgical instruments in different scenarios are different, the types and parameters are numerous, the parameters are highly correlated, and the safety coefficient requirement is high, the operational efficiency and accuracy of the laser surgical instruments are improved by the automatic error correction and communication de-redundancy based on the state memory mechanism on the basis of the HMI screen.

Optionally, after the target register is switched to the blocking state, the method further comprises: when the alarm clearing instructions sent by the laser surgical instrument are monitored, clearing the alarm information based on the logical operation rules and the alarm clearing instruction; and, when the clearing process is completed, triggering the target register to be switched from the blocking state to the non-blocking state, and generating a zeroing instruction, sending the zeroing instruction to the target register to cause the target register to perform zeroing processing according to the zeroing instruction. Thus, for the received alarm information of a non-internal alarm, the target register is first triggered to switch to the blocking state to block useless logic processing and redundant communication, and when the alarm clearing instruction sent by the peripheral instrument is received, the target register is triggered to switch to the non-blocking state, thereby avoiding useless logic processing and communication redundancy through the state memory mechanism and improving the operational efficiency and accuracy of the controller, and further improving the control efficiency and accuracy of the laser surgical instruments.

In summary, the method for controlling the laser surgical instrument provided by embodiments of the present application has the following advantages: (1) reducing the communication redundancy of the registers through logic operation rules, thereby improving the operation efficiency of the electronic device, and thereby further improving the operation efficiency of the laser surgical instrument; and (2) reducing the risk of errors by means of automatic error correction through state memory which ensures the accuracy and stability in the adjustment and control process of the multiple pieces of parameter information which has strong correlations, thus improving the control precision of the laser surgical instruments; (3) further improving the operational efficiency based on collaborative computation and task allocation mechanism in the relationship of hard-decoupling; (4) realizing independent development of software for each hardware carrier, as well as independent testing of each peripheral instrument, speeding up the development speed; (5) realizing operations between the underlying addresses and registers through the logical operation rules, which improves the software operation efficiency and reduces the occupied space of the software package, thus reducing the cost; (6) the system starts in seconds after power-on, without waiting time before surgery caused by power-on operation and so on; and, avoids the surgical risks caused by the problems such as blue screen and crash etc., which ensures the safety and efficiency of the laser surgery, so it has a good practical value, and is easy to promote the implementation in practical applications.

On the basis of FIG. 2 above, embodiments of the present application also provide another method for controlling laser surgical instruments, which focuses on describing a process of controlling a laser surgical instrument in laser surgery, specifically, pre-setting a surgical procedure set $M=\{m_1, m_2, \ldots, m_n\}$; a set of registers for variable arithmetic and logical judgments $X=\{x_1, x_2, \ldots, X_n\}$; the set of state memory registers $R=\{r_1, r_2, \ldots, r_n\}$; the set of variable storage addresses $P=\{p_1, p_2, \ldots, p_n\}$; the set of values pointed by the variable storage addresses $*P=\{*p_1, *p_2, \ldots, *p_n\}$. The parameter information set of the target surgical procedure m, comprises: adjustable surgical parameters 1 i.e. $a_{m_i}^1$, adjustable surgical parameters 2 i.e. $a_{m_i}^2$, non-adjustable surgical parameter 1 i.e. $b_{m_i}^1$, and adjustable surgical parameters 3 i.e. $a_{m_i}^3$; wherein, $b_{m_i}^1$ meets $f_1(a_{m_i}^1, a_{m_i}^2)=b_{m_i}^1$ and $b_{m_i}^1=[\min b_{m_i}^1, \max b_{m_i}^1]$; $a_{m_i}^3$ dynamically constraints the valid intervals of $a_{m_i}^1$ with different values.

Figure 3:
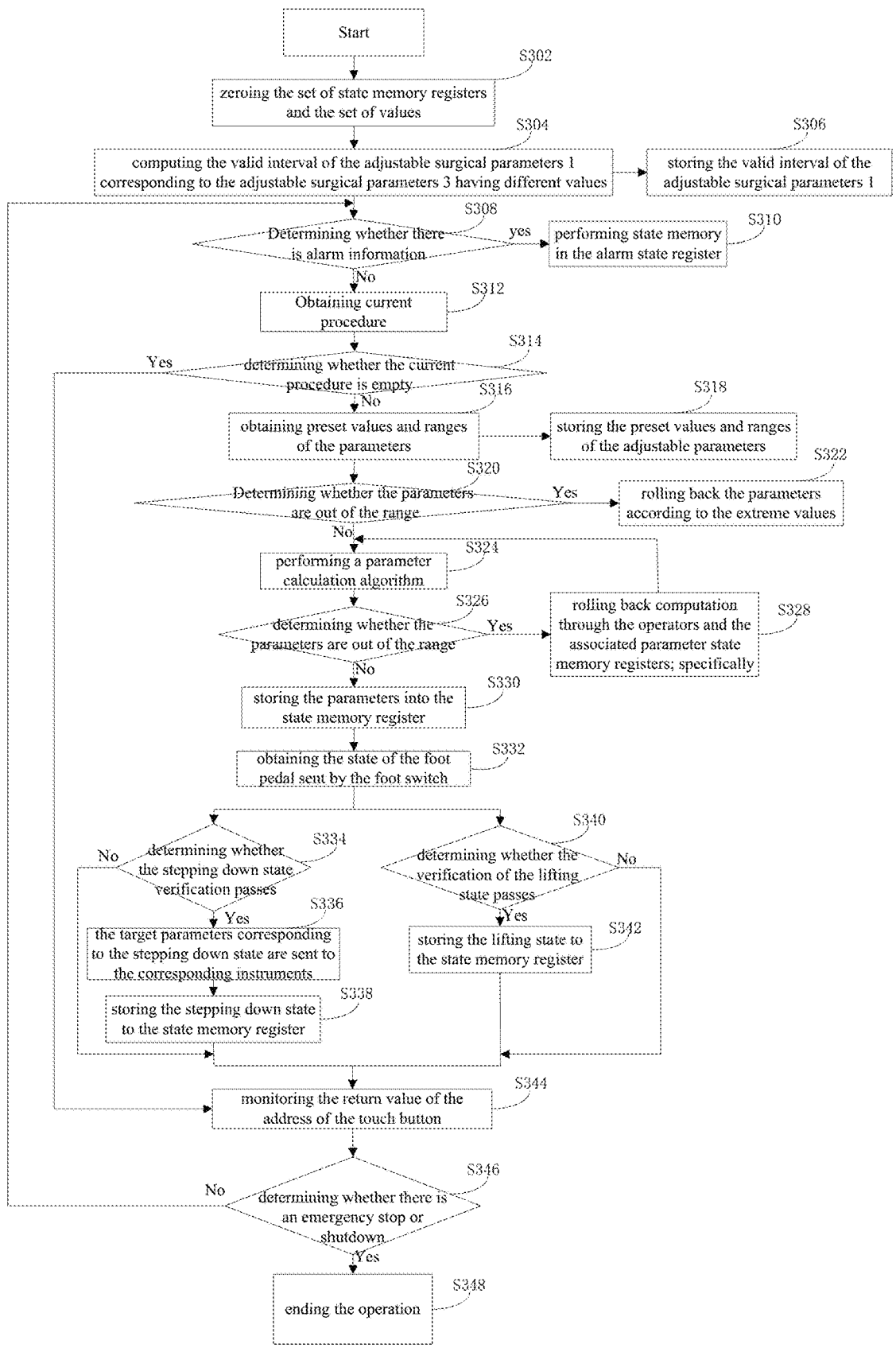
FIG. 3 shows a flow chart of another method for controlling the laser surgical instrument provided by embodiments of the present application.

As shown in FIG. 3, the method specifically includes the following steps:

Step S302, Zeroing the set of state memory registers and the set of values; that is, zeroing $R=\{r_1, r_2, \ldots, r_n\}$ and $*P=\{*p_1, *p_2, \ldots, *p_n\}$.

Step S304, computing the valid interval of the adjustable surgical parameters 1 corresponding to the adjustable surgical parameters 3 having different values; i.e., calculating $a_{m_i}^3=[\min a_{m_i}^3, \max a_{m_i}^3]$, $\min a_{m_i}^1$ and $\max a_{m_i}^1$ corresponding to all values of the accuracy to obtain the valid interval of the adjustable surgical parameters 1.

Step S306, storing the valid interval of the adjustable surgical parameters 1; specifically, storing the valid interval of the adjustable surgical parameters 1 in order at any self-defined starting address that does not conflict with other addresses, the length of which depends on $[\min a_{m_i}^3, \max a_{m_i}^3]$, the precision of $a_{m_i}^3$, and the number of elements of M.

The above steps S302~S306 complete the initialization preloading process.

Step S308, determining whether there is alarm information; if yes, executing step S310, and if no, executing step S312.

Step S310, performing state memory in the alarm state register; for example, when an abnormality of a sensor of the instrument is monitored by the controller, uploading the alarm code to the pre-set alarm storage address $p_{20}$, and copying the value pointed by $p_{20}$ to the register X for a logical judgment, and if $*P_{20}$ is 0, then skipping, and if $*P_{20}$ is an arbitrary alarm code, storing the alarm in the register $r_{20}$ and then the logical processing state is set to 0, 0 represents the blocking state, and then by modifying the system address stored in the page as the alarm page stored in the macro, which implements the forced switching to the alarm page; if the alarm has not been processed, $r_{20}$ will always be 0, so it will always be forced to remain in the alarm page to remind the processing of the alarm, and to block useless logic processing and communication redundancy, dynamic planning the implementation of each functional module.

The above steps S308~S310 realize collaborative computation and state memory on the system level, which reduce the risk of error, and ensure the accuracy and stability in the process of adjustment and control of the information of multiple parameters which are strongly correlated, thereby improving the control accuracy and operational efficiency of the laser surgical instrument.

Step S312, obtaining current procedure.

Step S314, determining whether the current procedure is empty; if yes, executing step S344; if no, executing step S316; for example, copying the value pointed by the surgical procedure address $p_{30}$ to register X for logical judgment, if $*P_{30}$ is 0, then skipping. If $*P_{30}$ is an enumerated value, such as $m_{1\vee 2\vee 3\vee}$ (i.e., $m_1$, $m_2$ and $m_3$ in the surgical procedure set described above), determining that the current procedure is the target surgical procedure; if $*p_{30}$ is a non-enumerated value, then initiating an internal alarm or directly performing zeroing operation and skipping according to situations.

Step S316, obtaining preset values and ranges of the parameters; here, the preset values of the parameters include the adjustable surgical parameters and non-adjustable surgical parameters, and the ranges of the parameters includes a valid interval corresponding to the adjustable surgical parameters and a valid interval corresponding to the non-adjustable surgical parameters.

Step S318, storing the preset values and ranges of the adjustable parameters; for example, the preset values of $a_{m_i}^1$ of the current surgical procedure are stored at $p_1$, the preset values of $a_{m_i}^2$ are stored at $p_2$, the preset values of $b_{m_i}^1$ are stored at $p_3$, the preset values of $a_{m_i}^3$ are stored at $p_4$, the preset values of $\max a_{m_i}^1$ are stored at $p_{10}$, the preset values of $\min a_{m_i}^1$ are stored at $p_{11}$, the preset values of $\max a_{m_i}^2$ are stored at $p_{10}$, the preset values of $\min a_{m_i}^2$ are stored at $p_{13}$, and the preset values of $\max b_{m_i}^1$ are stored at $p_{14}$. the preset values of $\min b_{m_i}^1$ are stored at $p_{15}$, the preset values of $\max a_{m_i}^1$ are $p_{16}$, the preset values of $\min a_{m_i}^3$ are $p_{17}$, wherein $[\min a_{m_i}^1, \max a_{m_i}^1]$ are constrained by $a_{m_i}^3$, the extreme values will be stored in order at any self-defined starting address that does not conflict with the other addresses, and the length is $\Sigma=2*(a_{m_i}^3$ the number of precision).

Step S320, determining whether the parameters are out of the range; specifically, checking whether $a_{m_i}^1$, $a_{m_i}^2$, and $a_{m_i}^3$ are at the boundary of the maximum interval in the adjustment and control process, such as by copying $p_1$, $p_2$ and $p_4$ to X, and determining whether $*P_1=[*P_{11}, *P_{10}]$, $*P_2=[*P_{13}, *P_{12}]$, $*P_4=[*P_{17}, *P_{16}]$ are met based on the logical operation rules; if yes, executing step S322, and if not, executing step S324.

Step S322, rolling back the parameters according to the extreme values; specifically, if the above $*P_1=[*P_{11}, *P_{10}]$, $*P_2=[*P_{13}, *P_{12}]$, $*P_4=[*P_{17}, *P_{16}]$ are not met, then if it is out of the range downwards and the minimum value is assigned, and if it is out of range upwards and the maximum value is assigned, thus to realize the rollback of the parameters, and return to the step S320 for iteration to prevent generating error parameters which are out of the range; it is to be noted that, according to the current value of $a_{m_i}^3$, it is also possible to obtain corresponding max $a_{m_i}^1$ and min $a_{m_i}^1$ in order, and if $*p_1 \ne [\min a_{m_i}^1, \max a_{m_i}^1]$, it will be processed in accordance with the above rollback method. The specific processing can be referred to in the foregoing part of the constraint examples, and the embodiments of the present application will not be repeated in detail herein.

Step S324, performing a parameter calculation algorithm; specifically, performing optimization on parameters according to the logical operation rules and the constraint relationships between the parameters.

Step S326, determining whether the parameters are out of the range; specifically, determining whether the parameters are out of the range during the calculation process according to the range, if yes, executing step S328, otherwise, executing step S330.

Step S328, rolling back computation through the operators and the associated parameter state memory registers; specifically, according to for example, according to the current $f_1(*p_1, *p_2)=b_{m_i}^1$, if $b_{m_i}^1=[\min b_{m_i}^1, \max b_{m_i}^1]$, then the current $a_{m_i}^1$ and $a_{m_i}^2$ are stored into $r_1$ and $r_2$, respectively; if $b_{m_i}^1 \ne [\min b_{m_i}^1, \max b_{m_i}^1]$, then determining the instantaneous $*p_1=r_1$ and $*P_2=r_2$, if $*p_1 \ne r_1$, then according to the out-of-range direction of $b_{m_i}^1$ the extreme value is assigned, and then performing the inverse computation of the extreme value of $a_{m_i}^1$ through the operators $f_1$ and $r_2$ and then overwriting, as well as rolling back $*p_1$, and then the final value of $a_{m_i}^1$ is stored into $r_1$; if $*p_2 \ne r_2$ then obtaining the extreme value according to the out-of-range direction of $b_{m_i}^1$, then performing the inverse computation of the extreme value of $a_{m_i}^2$ through the operators $f_1$ and $r_1$ and then overwriting, as well as rolling back $*p_2$, and then the final value of $a_{m_i}^2$ is stored into $r_2$ to ensure the correctness of each parameter. It should be noted that the above rollback process also returns to step S324 to repeat until the rollback process is completed.

Step S330, storing the parameters into the state memory register; it should be noted that the parameters currently stored are target parameters, such as target adjustable surgical parameters and target non-adjustable surgical parameters that meet the range etc., and the target parameters are sent to the corresponding instruments in order to control the operation of the instruments in accordance with the corresponding target parameters, which ensures that the communication content is brief, effective, and without redundancy, and improves the efficiency of control, and reduces the efficiency of errors at the software level of the laser surgical instruments, thereby ensuring the control accuracy of the instruments; furthermore, by memorizing the state of the target parameters, it can also serve to perform automatic rollback recovery when an abnormality occurs during subsequent re-modification of the parameters; at the same time, performing the operation of storing the target parameters in the event of power-down also ensures that the parameters can be quickly recovered if the instrument is abnormally powered down due to the loosening of the plug or other reasons; and, the target parameters may also be sent to the corresponding instruments at step S336, which may be set according to the actual situation.

It is to be noted that the aforesaid in the process of the target parameters being sent to the corresponding instruments, the accuracy of the target parameters being sent can also be ensured by adding physical buttons on the electronic device or setting virtual buttons on the HMI screen so that it can be confirmed manually when the parameters are sent.

Step S332, obtaining the state of the foot pedal sent by the foot switch; wherein the state of the foot pedal includes a lifting state and a stepping down state, i.e., during the operation of the laser surgical instruments, when the user steps on the foot switch or lifts it, the foot switch will generate a rising edge or a falling edge signal, and the lifting state or the stepping down state will be generated, and be sent to the controller to enable the controller to make a logical decision on the lifting state and the stepping down state, respectively; For the stepping down state, executing steps S334 to S338, and for the lifting state, executing steps S340 to S342.

Step S334, determining whether the stepping down state verification passes; if yes, executing step S336; if no, executing step S344; specifically, storing the stepping down state to $p_{40}$, and verifies the values of $*p_{40}$ and $r_9$, wherein the last pedal number that was stepped down is recorded in $r_9$, and if the verification is successful, executes the corresponding functional modules. For example, when the signal of the rising edge of the left pedal is stepped down is captured, that is, when the signal corresponding to the stepping down state is obtained, compare whether $r_9$ is 0 to confirm whether there is currently no other pedal stepped down, and when the left pedal is stepped down the execution start to assign $r_9$ with a value of 1, and in the same way, when the right pedal is stepped down assigns $r_9$ with a value of 2. The falling edge is triggered by the lifting of the left and right pedals, comparing the current recorded pedal number of $r_9$ with the falling edge corresponding to the pedal. If it is consistent, $r_9$ is set to 0, and skipping vice versa; by internally comparing and verifying all the pedal state signals based on the logic operation rules, it is possible to avoid erroneous commands or non-compliant operations of the pedals, thereby ensuring the safety of the target surgical procedure.

Step S336, the target parameters corresponding to the stepping down state are sent to the corresponding instruments; specifically, when the stepping down state passes the verification, the controller also performs logical processing based on the logical operation rules to generate the target parameters corresponding to each instrument in the stepping down state, and sends the target parameters to the corresponding instruments, so as to cause the instruments to operate in accordance with the target parameters; it is to be noted that here, the target parameters are for the other instruments except the foot pedal instruments, after the current numbered foot pedal is stepped down, corresponding processing need to be performed or corresponding parameters or settings etc. need to be set accordingly, and the target parameters are stored when powered-down, etc., which can be set according to the actual situation;

Step S338, storing the stepping down state to the state memory register; it should be noted that here, when storing the stepping down state to the state memory register, the corresponding pedal signal and the like are also stored, and the details can be referred to in step S334;

Step S340, determining whether the verification of the lifting state passes; if yes, executing step S342; if no, executing step S344; the specific verification process can refer to step S334, and the embodiment of the present application will not be discussed in detail here;

Step S342, storing the lifting state to the state memory register; here the state memory register for storing the lifting state can be the same as the state memory register for storing the stepping down state as described above, or they can be different, and the state memory register can be set according to the actual situation;

Step S344, monitoring the return value of the address of the touch button; wherein, by assigning values by address return for all touch buttons to realize the logical branch judgment of the value of the same variable address, thus to achieve the purpose of the button listening, including the alarm function and other service functions (e.g., switching procedures, parameter reading and modification, etc.), the details can be referenced to the foregoing embodiment, the embodiments of the present application will not describe in detail herein.

Step S346, determining whether there is an emergency stop or shutdown; if yes, executing step S348; otherwise, return to step S308 to repeat the above process.

Step S348, ending the operation.

In summary, the embodiments of the present application firstly implement hard decoupling among various different peripheral hardware (i.e., laser surgical instruments) through HMI screen, and on the basis of the hard decoupling, the electronic devices and the peripheral hardware perform collaborative computing, and a bidirectional task assignment between different hardware may be generated at any time node to correct or change each other's operation states and logic branches, and without interrupting its own operation to improve the system efficiency. For processing various types of logics such as interrupt operations, status reminders, automatic error correction and rollback of parameters, alarm information and feedback etc., the state memory mechanism can also be used, thus to prevent generating errors and redundancy which improves the efficiency and accuracy of the electronic device, and thus improves the control efficiency and accuracy of the laser surgical instrument.

Figure 4:
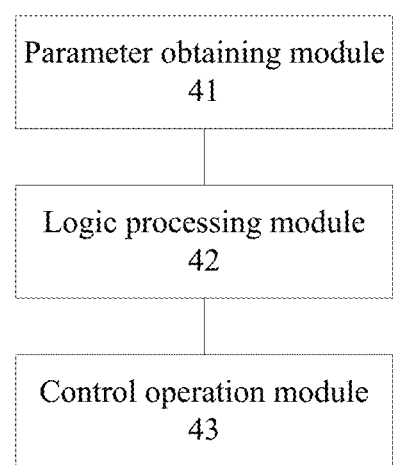
FIG. 4 shows a schematic diagram of an apparatus for controlling the laser surgical instrument provided by embodiments of the present application.

On the basis of the above method embodiments, embodiments of the present application also provide an apparatus for controlling the laser surgical instruments, applied to an electronic device configured with an HMI screen; wherein the electronic device further comprises a controller and registers, wherein the controller is communicatively connected to the HMI screen, the registers, and the laser surgical instrument, respectively, and wherein the HMI screen and the laser surgical instrument are hard-decoupled, and wherein the controller is configured with logical operation rules, the logical operation rules are configured to represent direct logic operations between variable storage address and the register in the electronic device. As shown in FIG. 4, the apparatus comprises a parameter obtaining module 41, a logic processing module 42, and a control operation module 43 connected in order; wherein the function of each module are as follows:

The parameter obtaining module 41 is configured to obtain a parameter information set of a target surgical procedure corresponding to the laser surgical instrument; wherein the parameter information set comprises parameter information of each instrument in the laser surgical instrument, the parameter information comprises: adjustable parameters and non-adjustable parameters, and a first valid interval corresponding to the adjustable parameters and a second valid interval corresponding to the non-adjustable parameters;

The logic processing module 42 is configured to perform optimization logic processing on the parameter information set based on the logic operation rules to obtain a target parameter set; wherein the target parameter set comprises target parameters corresponding to each instrument;

The control operation module 43 is configured to control each instrument to operate in accordance with corresponding target parameters until the target surgical procedure is completed.

The apparatus for controlling the laser surgical instrument provided by embodiments of the present application perform optimization logic processing of the parameter information set of the target surgical procedure by means of logical operation rules, and control each instrument in the laser surgical instruments to operate in accordance with the corresponding target parameters, which avoids frequent switching or operation of the HMI screen for controlling the laser surgical instruments, and improves the operation efficiency of the laser surgical instruments, while at the same time reduces the error rate of the laser surgical instruments; and, the electronic device realizes the operations between a variable storage address and the register through logical operation rules, which not only improves the operation efficiency, but also avoids the surgical risks caused by the blue screen and other problems, and thus improves the operation accuracy of the laser surgical instruments, thus improves the safety of the laser surgery, and facilitates the promotion and implementation in practical applications, and has a good practical value.

In one of the alternative embodiments, the above parameter information set comprises an adjustable parameter set and a non-adjustable parameter set; the above logic processing module 42 is further configured to: optimize the adjustable parameter set based on the logic operation rules and the set of first valid intervals, and obtain a target adjustable parameter set; wherein the target adjustable parameter set comprises target adjustable parameters corresponding to each instrument, and the set of first valid intervals includes a first valid interval corresponding to each adjustable parameter in the adjustable parameter set; optimizing the non-adjustable parameter set based on the logical operation rules and the set of second valid intervals to obtain the target non-adjustable parameter set; wherein the target non-adjustable parameter set comprises target non-adjustable parameters corresponding to each instrument, and the set of second valid intervals includes a second valid interval corresponding to each non-adjustable parameter in the non-adjustable parameter set.

In another alternative embodiment, the above logic processing module 42 is further configured to: determine whether a constraint relationship exists between the adjustable parameters and the non-adjustable parameters in the parameter information set; if yes, based on the logic operation rules and the constraint relationship, optimize the logic processing of the parameter information set to obtain the target parameter set.

Optionally, the aforesaid adjustable parameters comprise a first adjustable parameter and a second adjustable parameter, and the step of performing optimization logical processing of the parameter information set based on the logical operation rules and the constraint relationships comprises: if the first adjustable parameter changes, determining an out-of-range direction of the non-adjustable parameter based on the second valid interval corresponding to the non-adjustable parameter, and performing a reverse calculation based on the out-of-range direction, the second adjustable parameter, and the constraint relationship to obtain a target first adjustable parameter corresponding to the first adjustable parameter.

In another alternative embodiment, the above-described logic processing module 42 is further configured to: determine whether a constraint relationship exists between the adjustable parameters in the parameter information set; if yes, performing optimization logic processing on the parameter information set based on the logic operation rules and the constraint relationship to obtain the target parameter set.

Optionally, the above adjustable parameters include a third adjustable parameter and a fourth adjustable parameter, and the step of performing the optimization logic processing on the parameter information set based on the logical operation rules and the constraint relationship further comprises: if the third adjustable parameter is changed, and, if it does not exceed the corresponding first valid interval, determining a out-of-range direction of the fourth adjustable parameter based on the first valid interval corresponding to the fourth adjustable parameter, and determining the corresponding extreme value at the out-of-range direction as the target fourth adjustable parameter corresponding to the fourth adjustable parameter.

In another alternative embodiment, the above-described logic processing module 42 is further configured to: determine whether a constraint relationship exists between the non-adjustable parameters in the parameter information set; if yes, perform the optimization logic processing on the parameter information set based on the logic operation rules and the constraint relationship to obtain the target parameters set.

In another alternative embodiment, the above-described logic processing module 42 is further configured to: determine whether a constraint relationship exists between the adjustable parameters and the non-adjustable parameters, as well as between the adjustable parameters in the parameter information set; and if yes, perform optimization logic processing on the parameter information set based on the logic operation rules and the constraint relationship to obtain the target parameter set.

In another alternative embodiment, the above-described logic processing module 42 is further configured to: determine whether a constraint relationship exists between the adjustable parameters and the non-adjustable parameters, as well as between the non-adjustable parameters, in the parameter information set; if yes, perform optimization logic processing on the parameter information set based on the logic operation rules and the constraint relationship to obtain the target parameter set.

In another alternative embodiment, the above-described logic processing module 42 is further configured to: determine whether a constraint relationship exists between the adjustable parameters and the non-adjustable parameters, between the adjustable parameters, and between the non-adjustable parameters in the parameter information set; if yes, perform optimization logic processing on the parameter information set based on the logic operation rules and the constraint relationship to obtain the target parameter set.

In another alternative embodiment, the apparatus further comprises: obtaining an operation information set sent by the laser surgical instruments; wherein the operation information set comprises operation information sent by each instrument; determining target operation information based on the priority information carried by each piece of the operation information; performing logical processing on the target operation information based on the logical operation rules, and feeding the processing results back to the target instrument corresponding to the target operation information.

In another alternative embodiment, the variable storage address comprises an alarm storage address, and the apparatus further comprises: when alarm information is monitored at the alarm storage address, determining whether the alarm information is an internal alarm; wherein the internal alarm is alarm information generated by the electronic device; if yes, generating an alarm processing instruction based on the logical operation rules, and processing the alarm information based on the alarm processing instruction; and generating a reset instruction after the processing of the alarm information is completed, and the reset instruction is sent to the alarm storage address to cause the alarm storage address to be cleared and reset in accordance with the reset instruction.

In another alternative embodiment, the device further comprises: generating the blocking processing instruction based on the logic operation rules if the alarm information is a non-internal alarm; wherein the non-internal alarm is alarm information sent by the laser surgical instrument; sending the blocking processing instruction to a target register corresponding to the alarm storage address, so as to cause the target register to be switched to a blocking state according to the blocking processing instruction; wherein the target register is a state memory register.

In another alternative embodiment, after the aforesaid target register is switched to the blocking state, the apparatus further comprises: when the alarm clearing instruction sent by the laser surgical instrument is monitored, performing a clearing process on the alarm information based on the logical operation rules and the alarm clearing instruction; and, when the clearing process is completed, triggering the target register to be switched from the blocking state to the non-blocking state and generating a zeroing instruction, and sending the zeroing instruction to the target register to cause the target register to perform zeroing processing based on the zeroing instruction.

The apparatus for controlling the laser surgical instrument provided by the embodiments of the present application has the same technical features as the method for controlling the laser surgical instrument provided by the above-described embodiments, and therefore can also solve the same technical problems and achieve the same technical effects.

Embodiments of the present application also provide an electronic device comprising a processor and a memory, the memory stores instructions which can be executed by the processor, and the processor is configured to execute the instructions to realize the above-described method for controlling the laser surgical instruments.

Figure 5:
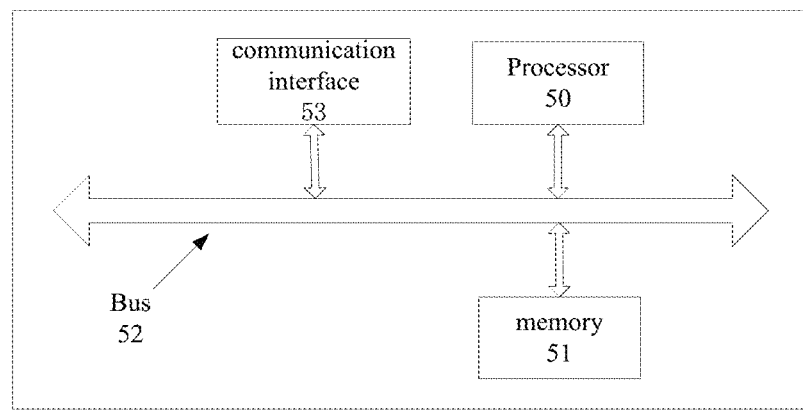
FIG. 5 shows a schematic diagram of the structure of an electronic device provided by embodiments of the present application.

Referring to FIG. 5, the electronic device comprises a processor 50 and a memory 51, the memory 51 stores machine-executable instructions which can be executed by the processor 50, the processor 50 executes the machine-executable instructions to implement the above-described method for controlling the laser surgical instruments.

Further, the electronic device shown in FIG. 5 further comprises a bus 52 and a communication interface 53, wherein the processor 50, the communication interface 53 and the memory 51 are connected via the bus 52.

Wherein the memory 51 may comprise a high-speed random access memory (RAM, Random Access Memory) or a non-volatile memory (non-volatile memory), such as at least one disk memory. A communication connection between this system network element and at least one other network element is realized through at least one communication interface 53 (which may be wired or wireless), which may use the Internet, a wide area network, a local network, a metropolitan area network, and so on. The bus 52 may be an ISA (Industrial Standard Architecture) bus, a PCI (Peripheral Component Interconnect) bus or an EISA (Enhanced Industry Standard Architecture) bus, PCI (Peripheral Component Interconnect) bus, or EISA (Enhanced Industry Standard Architecture) bus. The above buses can be categorized into address buses, data buses, control buses, and so on. For ease of representation, only one bi-directional arrow is shown in FIG. 5, which does not mean that there is only one bus or one type of bus.

The processor 50 may be an integrated circuit chip with signal processing capability. In implementation, the steps of the method described above may be accomplished by integrated logic circuits of hardware in the processor 50 or by instructions in the form of software. The above-described processor 50 may be a general-purpose processor, including a central processing unit (Central Processing Unit, or CPU for short), a network processor (Network Processor, or NP for short), etc.; it may also be a digital signal processor (Digital Signal Processor, or DSP for short), an Application Specific Integrated Circuit (Application Specific Integrated Circuit, or ASIC for short), Field-Programmable Gate Array (Field-Programmable Gate Array, or FPGA for short), or other programmable logic devices, discrete gates or transistor logic devices, and discrete hardware components. Various methods, steps, and logic block diagrams in the embodiments of the present application may be implemented or performed. The general purpose processor may be a microprocessor or the processor may also be any conventional processor, etc. The steps of the methods in the embodiments of the present application may be directly implemented in a hardware decoding processor, or be implemented with a combination of the hardware and software modules in the decoding processor. The software module may be located in a random memory, flash memory, read-only memory, programmable read-only memory or electrically erasable programmable memory, registers, and other storage media well established in the art. The storage medium is located in a memory 51, and the processor 50 reads the information in the memory 51 to accomplish the steps of the methods of the preceding embodiments in combination with the hardware.

This embodiment also provides a machine-readable storage medium, the machine-readable storage medium storing machine-executable instructions, the machine-executable instructions, when invoked and executed by the processor, causes the processor to implement the aforementioned methods for controlling the laser surgical instrument.

The computer program product of the electronic device, apparatus and method for controlling the laser surgical instruments provided by the embodiments of the present application comprises a computer-readable storage medium storing program code, and said program code comprises instructions that can be used to execute the methods described in the preceding method embodiments, the specific implementation of which can be found in the method embodiments and will not be repeated herein.

Those skilled in the field can clearly understand that, for the convenience and conciseness of the description, the specific working process of the above-described systems and apparatuses can be referred to the corresponding processed in the preceding method embodiments, and will not be repeated herein.

In addition, in the description of the embodiments of the present application, unless otherwise expressly provided and limited, the terms "mounted", "coupled", and "connected" shall be broadly construed as, for example, a fixed connection, a detachable connection, or an integrated connection, it may also be a mechanical connection or an electrical connection; it may be a direct connection or an indirect connection through an intermediate medium; it may be a connection within two elements. For a person skilled in the art, the specific meaning of the above terms in the present application may be understood according to specific situations.

Said functions, when implemented as a software functional unit and sold or used as a stand-alone product, may be stored in a processor-executable, non-volatile, computer-readable storage medium. Based on this understanding, the technical solutions of the present application which is essentially or in part a contribution to the prior art, or part of the technical solutions may be embodied in the form of a software product, the computer software product is stored in a storage medium and comprises a plurality of instructions to cause a computer device (which may be a personal computer, a server, or a network device, etc.) to carry out all or part of the steps of the methods described in the various embodiments of the present application. The aforementioned storage medium includes a USB flash drive, a removable hard disk, a read-only memory (ROM, Read-Only Memory), a random access memory (RAM, Random Access Memory), a diskette or a CD-ROM, and other media that can store program code.

In the description of this application, it is noted that the orientation or position relationship indicated by the terms "center", "top", "bottom", "left", "right", "vertical", "horizontal", "inner", "outer" etc. are based on those shown in the accompanying drawings, and are intended only to facilitate the description of the present application and to simplify the description, and are not intended to indicate or imply that the apparatus or element referred to must be constructed and operated with the particular orientation, and therefore are not to be construed as a limitation of the present application. Furthermore, the terms "first", "second", and "third" are used for descriptive purposes only and are not to be understood as indicating or implying relative importance.

Finally, it should be noted that the above-described embodiments are only specific embodiments of the present application, which are used to illustrate the technical solutions of the present application rather than to limit the scope of protection of the present application, and the scope of protection of the present application is not limited thereto, and although the present application has been described in detail with reference to the aforesaid embodiments, the person skilled in the art should understand that, any person of skill familiar with the field of the present application can still modify or make changes without efforts to the technical solutions disclosed in the foregoing embodiments, or make equivalent replacements for some of the technical features therein; and these modifications, changes or replacements do not make the essence of the corresponding technical solutions depart from the spirit and scope of the technical solutions of the embodiments of the present application, and shall be covered by the scope of protection of the present application. Therefore, the scope of protection of the present application shall be stated to be subject to the scope of protection of the claims.

INDUSTRIAL APPLICABILITY

The method, apparatus and electronic device for controlling laser surgical instruments provided by the embodiments of the present application can avoid frequent switching or operation of the HMI screen to control the laser surgical instruments, which improves the operation efficiency of the laser surgical instruments, and at the same time reduces the error rate of the laser surgical instruments, which is of good practical value.

The invention claimed is:

1. A method of controlling laser surgical instruments, applied to an electronic device equipped with an HMI screen, wherein said electronic device further comprises a controller and a register, said controller being communicatively connected to the HMI screen, the register, and the laser surgical instruments, respectively, said HMI screen being hard-decoupled with the laser surgical instruments, and the controller being configured with logical operation rules, said logical operation rules configured to represent direct logical operations between a variable storage address and the register in said electronic device, said method comprising:

obtaining a parameter information set for a target surgical procedure corresponding to the laser surgical instruments; wherein said parameter information set comprises parameter information for each of the laser surgical instruments, said parameter information comprising: adjustable parameters and non-adjustable parameters, and a first valid interval corresponding to the adjustable parameters and a second valid interval corresponding to the non-adjustable parameters;

performing optimization logic processing on the parameter information set based on the logical operation rules to obtain a target parameter set, wherein the target parameter set comprises target parameters corresponding to each of the laser surgical instrument;

controlling each of the laser surgical instruments to operate in accordance with the corresponding target parameters until the target surgical procedure is completed, wherein the variable storage address comprises an alarm storage address, the method further comprising:

when alarm information is monitored at the alarm storage address, determining whether the alarm information is an internal alarm; wherein the internal alarm is alarm information generated by the electronic device;

if yes, generating an alarm processing instruction based on the logical operation rules and processing said alarm information in accordance with the alarm processing instruction; and, generating a reset instruction after the processing is completed and sending the reset instruction to the alarm storage address to cause the alarm storage address to be cleared and reset in accordance with the reset instruction, wherein the method further comprises:

generating a blocking processing instruction based on the logical operation rules if the alarm information is a non-internal alarm, wherein the non-internal alarm is alarm information sent by the laser surgical instruments;

sending the blocking processing instruction to a target register corresponding to the alarm storage address to cause the target register to switch to a blocking state based on the blocking processing instruction, wherein the target register is a state memory register.

2. The method according to claim 1, wherein the parameter information set comprises an adjustable parameter set and a non-adjustable parameter set; and the step of performing optimization logic processing of the parameter information set based on the logical operation rules comprises:

optimizing the adjustable parameter set based on the logical operation rules and the first valid interval set to obtain a target adjustable parameter set; wherein the target adjustable parameter set comprises target adjustable parameters corresponding to each of the laser surgical instruments, the first valid interval set comprises the first valid interval corresponding to each adjustable parameter in the adjustable parameter set;

optimizing the non-adjustable parameter set based on the logical operation rules and the second valid interval set to obtain a target non-adjustable parameter set; wherein the target non-adjustable parameter set comprises target non-adjustable parameters corresponding to each of the laser surgical instruments, the second valid interval set comprises the second valid interval corresponding to each non-adjustable parameter in the non-adjustable parameter set.

3. The method according to claim 1, wherein the step of performing optimization logic processing of the parameter information set based on the logical operation rules comprises:

determining whether there is a constraint relationship in the parameter information set, the constraint relationship comprises: a constraint relationship between the adjustable parameters and the non-adjustable parameters; and/or a constraint relationship between the adjustable parameters; and/or a constraint relationship between the non-adjustable parameters;

if yes, performing optimization logic processing on the parameter information set based on the logical operation rules and the constraint relationship, to obtain the target parameter set.

4. The method according to claim 1, wherein the method further comprises:

obtaining an operation information set sent by the laser surgical instruments; wherein the operation information set comprises operation information sent by each of the laser surgical instruments;

determining target operation information based on priority information carried by each of the operation information;

performing optimization logic processing on the target operation information based on the logical operation rules and feeding processing results to the target instrument corresponding to the target operation information.

5. The method according to claim 1, wherein after the target register is switched to the blocking state, the method further comprises:

when an alarm clearing instruction sent by the laser surgical instruments is monitored, performing clearing processing of the alarm information based on the logical operation rules and the alarm clearing instruction; and, when the clearing processing is completed, triggering the target register to switch from the blocking state to a non-blocking state, and generating a zeroing instruction, sending said zeroing instruction to the target register to cause the target register to carry out zeroing processing based on the zeroing instruction.

6. An apparatus for controlling laser surgical instruments, applied to an electronic device equipped with an HMI screen, wherein said electronic device further comprises a controller and a register, the controller being communicatively connected to the HMI screen, the register and the laser surgical instrument, respectively, and the HMI screen being hard-decoupled with the laser surgical instruments, and the controller being configured with logical operation rules, the logical operation rules being configured to represent direct logical operations between a variable storage address and the register in the electronic device, the apparatus comprising:

a parameter obtaining module configured to obtain a parameter information set for a target surgical procedure corresponding to the laser surgical instruments, wherein the parameter information set comprises parameter information for each of the laser surgical instruments, the parameter information comprising: adjustable parameters and non-adjustable parameters, a first valid interval corresponding to the adjustable parameters and a second valid interval corresponding to the non-adjustable parameters;

a logic processing module configured to perform optimization logic processing on the parameter information set based on the logic operation rules to obtain a target parameter set; wherein the target parameter set comprises target parameters corresponding to each of the laser surgical instruments;

a control operation module configured to control each of the laser surgical instruments to operate in accordance with the corresponding target parameters until the target surgical procedure is completed, wherein the variable storage address comprises an alarm storage address, the apparatus further comprising:

when alarm information is monitored at the alarm storage address, determining whether the alarm information is an internal alarm; wherein the internal alarm is alarm information generated by the electronic device;

if yes, generating an alarm processing instruction based on the logical operation rules and processing said alarm information in accordance with the alarm processing instruction; and, generating a reset instruction after the processing is completed and sending the reset instruction to the alarm storage address to cause the alarm storage address to be cleared and reset in accordance with the reset instruction;

wherein the method further comprises:

generating a blocking processing instruction based on the logical operation rules if the alarm information is a non-internal alarm, wherein the non-internal alarm is alarm information sent by the laser surgical instruments;

sending the blocking processing instruction to a target register corresponding to the alarm storage address to cause the target register to switch to a blocking state based on the blocking processing instruction, wherein the target register is a state memory register.

7. An electronic device comprising a memory, a processor and computer program stored on the memory and executable by the processor, wherein the steps of the method in claim 1 are implemented when the computer program is executed by the processor.

8. A computer-readable storage medium, wherein the computer-readable storage medium has computer program stored thereon and the computer program when executed by the processor implements the steps of the method in claim 1.

* * * * *